United States Patent [19]

Warner, Jr. et al.

[11] 4,375,545

[45] Mar. 1, 1983

[54] PROCESS FOR THE SYNTHESIS OF THE NICOTINYL ESTER OF 6-AMINONICOTINIC ACID

[75] Inventors: Paul L. Warner, Jr., Clarence; Edward J. Luber, Jr.; William A. Somerville, both of Buffalo; F. Christopher Zusi, Williamsville, all of N.Y.

[73] Assignee: Westwood Pharmaceuticals, Inc., Buffalo, N.Y.

[21] Appl. No.: 275,577

[22] Filed: Jun. 22, 1981

[51] Int. Cl.$^3$ .............................................. C07D 213/79
[52] U.S. Cl. ................................................... 546/263
[58] Field of Search ......................................... 546/263

[56] References Cited

U.S. PATENT DOCUMENTS 4,031,104  6/1977  Bossert et al. ...................... 546/263

Primary Examiner—Henry R. Jiles
Assistant Examiner—Robert C. Whittenbaugh
Attorney, Agent, or Firm—Morton S. Simon

[57] ABSTRACT

6-Aminonicotinic acid is reacted with an alkali carbonate selected from the group consisting of sodium carbonate and potassium carbonate. The reaction is carried out at elevated temperature and in dimethylformamide. The 6-aminonicotinic acid alkali salt so produced is reacted with 3-chloromethylpyridine hydrochloride. The reaction is carried out at elevated temperature and in dimethylformamide. The desired nicotinyl ester is thus produced.

4 Claims, No Drawings

PROCESS FOR THE SYNTHESIS OF THE NICOTINYL ESTER OF 6-AMINONICOTINIC ACID

BACKGROUND OF THE INVENTION

1. Field of the Invention

This invention relates to a method of producing the nicotinyl ester of 6-aminonicotinic acid. More particularly, the invention relates to a method of producing such ester in high yield.

2. Description of the Prior Art

U.S. Pat. No. 4,141,977, issued Feb. 2, 1979 to Eugene Van Scott and Ruey J. Yu, discloses 6-substituted nicotinic acid and its esters when topically applied are useful in alleviating the symptoms of psoriasis. The 6-aminonicotinic acid methyl ester, the ethyl ester, the tert. butyl ester and the nicotinyl ester are specifically disclosed. In col. 5, lines 59 et seq. of the patent, a method of synthesis of the ethyl ester is set forth. The method results in the production of an amount of 6-aminonicotinic acid ethyl ester corresponding to a yield of 82% based on the weight of the starting materials. One skilled in the art would appreciate that if this method were utilized to produce the nicotinyl ester, a substantially lower, unacceptable, yield would result.

U.S. Pat. No. 2,199,839, issued May 7, 1940 to Raemer R. Renshaw and Paul F. Dreisbach, also discloses the synthesis of a variety of lower alkyl esters of 6-aminonicotinic acid by the method of Fischer esterification. Again, one skilled in the art would appreciate that a substantial yield of the nicotinyl ester of 6-aminonicotinic acid could not be obtained through use of this method. The hydrogen chloride gas would react with the nicotinyl alcohol to form an intractable mass. U.S. Pat. No. 2,199,839 further discloses reaction of the potassium salt of 6-aminonicotinic acid with 2-chloroethyldiethyl amine by heating both components on a steam bath in the absence of solvent. The present inventors similarly reacted the potassium salt of 6-aminonicotinic acid with 3-chloromethylpyridine. No yield whatsoever of nicotinyl ester of 6-aminonicotinic acid resulted. Only a tar was obtained.

Thus, there is need for development of a synthetic method for producing the nicotinyl ester of 6-aminonicotinic acid in high yield.

DISCLOSURE OF INVENTION

According to the method of the present invention 6-aminonicotinic acid is reacted with an alkali carbonate selected from the group consisting of sodium carbonate and potassium carbonate. The reaction is carried out at elevated temperature and in dimethylformamide. The 6-aminonicotinic acid alkali salt so produced is reacted with 3-chloromethylpyridine hydrochloride. The reaction is carried out at elevated temperature and in dimethylformamide. The nicotinyl ester of 6-aminonicotinic acid is thus produced.

Various solvents have been evaluated as reaction solvents in the above-described synthesis of the present invention. Water, dimethoxyethane, acetone/water mixture, dioxane, dimethylsulfoxide, ethanol and acetonitrile when used as the reaction solvent resulted in the production of the nicotinyl ester in unacceptably low yields. Surprisingly, of the numerous solvents tested, only dimethylformamide enabled attainment of the desired high yield of the nicotinyl ester.

As alkali carbonate, one can employ sodium carbonate or potassium carbonate. The highest yield is attainable with sodium carbonate. Potassium carbonate results in a substantially lower yield. We have determined that, at a reaction temperature of 100° C., with use of sodium carbonate as a reactant, there is an almost twofold increase in yield of the nicotinyl ester as compared with use of an equimolar amount of potassium carbonate reaction product. This is indeed surprising and unexpected.

The reaction is desirably carried out at elevated temperature. Preferably, the temperature ranges from about 80° C. to reflux temperature. More preferably, the temperature is from about 100° C. to reflux temperature. Most preferably the temperature is reflux temperature.

The present inventors have found that surprisingly, as the reaction temperature is increased from 80° C. to 100° C., the yield rises and peaks at 100° C. The yield then falls between 100° C. to 140° C. Then, surprisingly, and unexpectedly, there is a sharp increase in yield as the temperature is increased from 140° C. to reflux temperature. In point of fact, over this very short temperature span, the yield dramatically and unexpectedly increases approximately 25%.

In the step of reacting the alkali salt of 6-aminonicotinic acid, 3-chloromethylpyridine hydrochloride or other suitable salt thereof may be employed as co-reactant. Preferably, 3-chloromethylpyridine hydrochloride is utilized.

The invention will now be illustrated and described in greater detail with reference to the examples which follow:

EXAMPLE 1

414.4 g (3.0 moles) 6-aminonicotinic acid and 414.6 g (3.0 moles) potassium carbonate are added to 5.5 liters N,N-dimethylformamide ("DMF") in a 12 liter three-necked round bottom reaction flask equipped with a stirrer. The reaction mixture is stirred mechanically, refluxed for about 60 hours, then cooled to 100° C. Then, while maintaining the reaction mixture at a temperature of 100° C., 492.2 g (3.0 moles) 3-chloromethylpyridine hydrochloride are incrementally added thereto over a period of one hour. The reaction temperature of 100° C. is maintained for an additional hour. Then, the DMF is removed by concentrating the reaction mixture to about 1 liter by distillation in vacuo and 3 liters of ice are added to the cooled reaction mixture. The suspension which results is diluted to 3.5 liters with water and the resultant product collected and washed repeatedly with water until the washings are nearly colorless. The product is dried and then recrystallized from toluene (12.5 liters) whereby 236.6 g (representing a yield of 34.4%) of the nicotinyl ester of 6-aminonicotinic acid ($C_{12}H_{11}N_3O_2$, M.W.=229.24, m.p. 142°-143.5° C.) are obtained. The reaction scheme is depicted as follows:

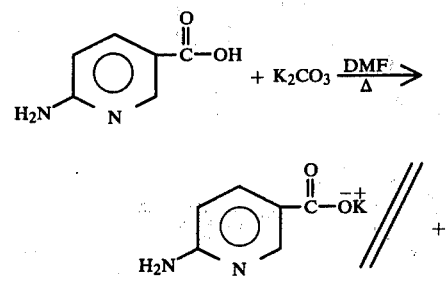

-continued

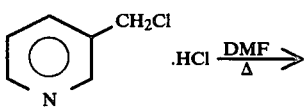

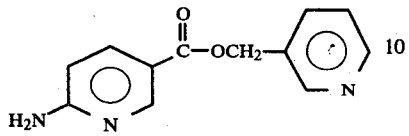

EXAMPLE 2

414.4 g (3.0 moles) 6-aminonicotinic acid and 318 g (3.0 moles) sodium carbonate are added to 5.5 liters of N,N-dimethylformamide ("DMF") in a 12 liter three-necked round bottomed flask equipped with a stirrer. The reaction mixture is stirred mechanically and refluxed vigorously for at least 1 to 1½ hours. During this time, the contents of the reaction flask thicken considerably. The reaction mixture is cooled to 140° C. and while this temperature is maintained, 492.2 g (3.0 moles) 3-chloromethylpyridine hydrochloride are added over a period of one hour and at a rate of approximately 8.2 g/min. After the addition of the 3-chloromethylpyridine hydrochloride is complete, the reaction mixture is heated to reflux and maintained at reflux temperature for one hour. Thereafter, the reaction mixture is concentrated in vacuo to about 1 liter. Then, 3 liters of ice are added to the concentrate. The mixture so produced is stirred and diluted with water to a total volume of 3.5 liters. The brown solid which results is collected, washed with water, resuspended in 2.5 liters of an ice-/water mixture and then once again collected. This procedure is repeated until the washings are nearly colorless, at which point the product is collected and dried completely in vacuo whereby 572.7 g of crude nicotinyl ester of 6-aminonicotinic acid are obtained. Recrystallization of this product from toluene (15 liters) affords 527.3 g (representing a yield of 76.76%) of pure nicotinyl ester of 6-aminonicotinic acid ($C_{12}H_{11}N_3O_2$, M.W.=229.24, m.p. 142°–143.5° C.). The reaction scheme is depicted as follows:

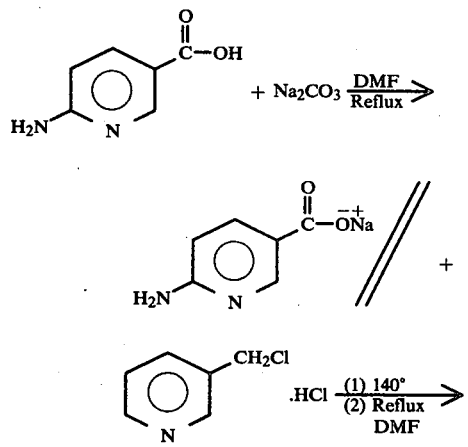

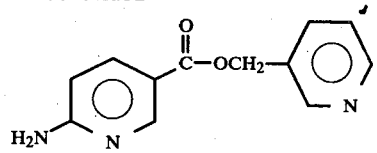

EXAMPLE 3

Example 2 is repeated, except the reaction of 6-aminonicotinic acid with sodium carbonate and the subsequent reaction with 3-chloromethylpyridine hydrochloride are carried out at a temperature of 80° C. 330.5 g (representing a yield of 48.09%) of the nicotinyl ester of 6-aminonicotinic acid are obtained.

EXAMPLE 4

Example 2 is repeated, except the reaction of 6-aminonicotinic acid with sodium carbonate and the subsequent reaction with 3-chloromethylpyridine hydrochloride are carried out at a temperature of 100° C. 470.6 g (representing a yield of 68.43%) of the nicotinyl ester of 6-aminonicotinic acid are obtained.

EXAMPLE 5

Example 2 is repeated, except the reaction of 6-aminonicotinic acid with sodium carbonate and the subsequent reaction with 3-chloromethylpyridine hydrochloride are carried out at a temperature of 120° C. 445 g (representing a yield of 64.75%) of the nicotinyl ester of 6-aminonicotinic acid are obtained.

EXAMPLE 6

Example 2 is repeated, except the reaction of 6-aminonicotinic acid with sodium carbonate and the subsequent reaction with 3-chloromethypyridine hydrochloride are carried out at a temperature of 140° C. 423.6 g (representing a yield of 61.64%) of the nicotinyl ester of 6-aminonicotinic acid are obtained.

The results of examples 1–6 clearly demonstrate that sodium carbonate is most preferred; potassium carbonate is next preferred.

A comparison of the results of Examples 3 and 4 shows that all conditions being equal, use of potassium carbonate as a reactant results in a yield of 34.4% of the desired nicotinyl ester. In contrast thereto, when sodium carbonate is employed as a reactant, the nicotinyl ester is produced in a yield of 68.43%. This two-fold increase is indeed surprising and unexpected.

The examples further demonstrate that although the process is operative at elevated temperature, a range of about 80° C. to reflux temperature is preferred, a range of about 100° C. to reflux temperature is more preferred, and reflux temperature is most preferred.

Examples 3 and 4 demonstrate that as the reaction temperature is raised from 80° C. to 100° C., the yield rises rapidly. The reaction temperature peaks at 100° C., then starts to fall from 100°–140° C., then, surprisingly and unexpectedly, there is a sharp increase in yield as the temperature rises from 140° C. to reflux temperature.

Over this very short temperature span, the yield increases from 61.64% to 76.76%. This represents a dramatic and unexpected increase in yield of about 24.5%.

What is claimed is:

1. A process for producing 6-aminonicotinic acid nicotinyl ester comprising the steps of
   (a) reacting 6-aminonicotinic acid with an equimolar amount of sodium carbonate, in dimethylformamide and at an elevated temperature, to produce the corresponding sodium salt of 6-aminonicotinic acid;
   (b) then, reacting said salt with 3-chloromethylpyridine hydrochloride in dimethylformamide and at an elevated temperature, to produce said nicotinyl ester.

2. The process, as claimed in claim 1, wherein in step (b) the reaction is carried out at a temperature of from about 80° C. to reflux temperature.

3. The process, as claimed in claim 1, wherein in step (b) the reaction is carried out at a temperature of from about 100° C. to reflux temperature.

4. The process, as claimed in claim 1, wherein in step (b) the reaction is carried out at reflux temperature.

* * * * *